United States Patent [19]

Akakawa

[11] Patent Number: Plant 6,692

[45] Date of Patent: Mar. 21, 1989

[54] CLEMATIS PLANT NAMED ENA

[75] Inventor: Hiroshi Akakawa, Misato, Japan

[73] Assignee: Sakata Seed America, Inc., San Francisco, Calif.

[21] Appl. No.: 110,889

[22] Filed: Oct. 21, 1987

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A cultivar of Clematis named Ena, having very large, pale violet flowers, compact growth habit, excellent keeping qualities, and its adaptability to be grown in outdoor or pot programs.

1 Drawing Sheet

The present invention relates to a new and distinct cultivar of Clematis plant known by the cultivar name Ena.

Flower-bearing Clematis plants are one of the most spectacular of all flowering vines, and relatively easy to grow and maintain. The genus Clematis is very large, having as many as perhaps 300 different species. The species of Clematis which comprises the present invention is a perennial and well-known for bedding purposes.

Traditionally, Clematis have been used as bedding plants or climbers due to the vine characteristics of the species. The development of varieties for pot plant culture has accordingly centered around vine cultivars, with less than fully satisfactory results.

With the foregoing in mind, a breeding program was established by applicant in Nagano, Japan, the specific purpose of which was to develop a perennial Clematis that could be used both as a bedding plant and in pot plant programs. Applicant was particularly interested in developing a new cultivar that could exhibit consistently good and uniform pot performance, with a similar flowering season as outdoor cultivars.

Ena was originated from a hybridization made in 1974 in the controlled breeding program in Nagano, Japan referred to above. The male and female parents were cultivars in commercial production at that time and are not specifically identifiable at this time. The new cultivar Ena resulted from the selection and reselection by applicant of plants constituting the progeny of the stated parentage, and was selected primarily for its excellent pot performance and its large, light violet-blue flowers.

The first act of asexual reproduction of Ena was subsequently accomplished when cuttings were taken from the finally selected plant of the progeny of the stated cross by applicant in a controlled environment in Nagano, Japan. Horticultural examination of the plant resulting from asexual reproduction has demonstrated that the combination of characteristics as herein disclosed for Ena are firmly fixed and are retained through successive generations of asexual reproduction.

Ena has not been observed under all possible environmental conditions. The phenotype may vary significantly with variations in environment such as temperature, light intensity, and day length. The following observations, measurements and comparisons describe plants grown in Nagano, Japan under growing conditions which are similar to those generally used in commercial practice.

The following traits have been repeatedly observed and are determined to be basic characteristics of Ena, which in combination distinguish this Clematis as a new and distinct cultivar;

(1) Ena has a relatively compact habit when grown in a pot, with its height being approximately 10–15". Its growth habit is excellent.

(2) The overall flower size is very large, being 6–7 inches in diameter. The flower color is a pale violet blue.

(3) The stamens at the center of the flower are yellowish white, and the number and radial dimensions of the stamens from the center of the plant provide an attractive contrast with the flower petals.

(4) The number of flower petals varies from 6 to 8, and the petals are generally flat but slightly ruffled when the flower is fully open.

(5) The new cultivar can be grown outdoors as a bedding plant, or in pot plant programs. The normal blooming period for Ena when grown outdoors is May and June, and then again in September. These blooming periods can be duplicated when Ena is grown indoors in pot plant programs.

(6) Ena has short internodes, with the node at previous shoots evolving into a flower bud.

(7) The keeping qualities of the flowers of Ena are excellent, perhaps better than known cultivars.

In view of its unique characteristics as described above, it is difficult to compare Ena with currently available Clematis cultivars. The cultivar Hakuba was similarly bred for pot culture, and is disclosed in a pending application. In comparison to Hakuba, Ena has substantially larger flowers, pale violet flower color, a compact but not dwarf growth habit, and somewhat better flower keeping qualities.

The accompanying color photographic drawing shows typical inflorescence and foliage characteristics of Ena, with colors being as nearly true as possible with illustrations of this type. The photograph comprises a top perspective view of the new cultivar, and several of the unique characteristics of the new cultivar will be clearly apparent.

In the following description, color references are made to The Royal Horticultural Society Colour Chart, except where color designations of ordinary dictionary significance are used. The color values were determined at Nagano, Japan.

Classification:

*Botanical.*—Clematis cv. Ena.

*Commercial.*—Clematis.

Parentage:

*Male parent.*—Unknown.

*Female parent.*—Unknown.

Plant:

*Form and size.*—Symmetrical in form. The flower stems are of a length to produce a canopy of very large flowers above the foliage. The typical height of the plant when grown as a pot is 10–15 inches.

*Growth habit.*—Excellent; compact.

*Foliage.*—Size: Average. Quantity: Abundant. Color: Dark green, upper surface approximately 139A; veins light green and visible on upper surface. Shape: Generally heart-shaped. Texture: Dull.

Flowers:

*Form.*—Generally round, with 6–8 petals of equal size.

*Size.*—Overall diameter 6–7 inches, very large.

*Borne.*—On relatively short stems, above the foliage.

*Quantity.*—Floriferous.

*Blooming period.*—In outdoor plantings in Nagano, Japan blooming periods are May-June and again in September; in greenhouse pot culture, same flowering periods can be achieved.

*Color.*—Fully open, upper surface of petals — 92C, with lighter shades near longitudinal axes of petals.

*Reproductive organs.*—Stamens are whitish yellow and extend radially outwardly from the center and form an attractive flower center in contrast to the color of the petals; reproductive organs otherwise normal.

I claim:

1. A new and distinct cultivar of Clematis named Ena, as illustrated and described.

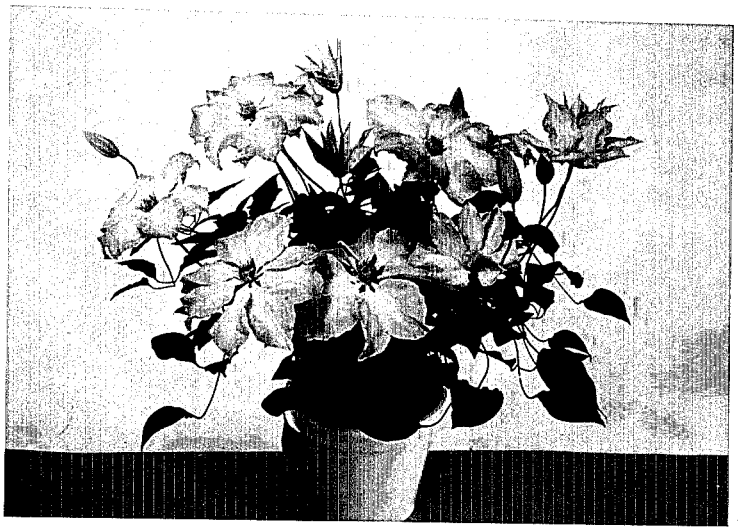

* * * * *